United States Patent [19]

Rippon

[11] Patent Number: 5,795,354
[45] Date of Patent: Aug. 18, 1998

[54] PROCESS FOR DYEING WOOL AND OTHER KERATIN FIBRES

[75] Inventor: John Anthony Rippon, Victoria, Australia

[73] Assignee: Commonwealth Scientific and Industrial Research Organization, Australian Capital Territory, Australia

[21] Appl. No.: 423,472

[22] PCT Filed: Mar. 25, 1988

[86] PCT No.: PCT/AU88/00086

§ 371 Date: Sep. 25, 1989

§ 102(e) Date: Sep. 25, 1989

[87] PCT Pub. No.: WO88/07602

PCT Pub. Date: Oct. 6, 1988

[30] Foreign Application Priority Data

Mar. 25, 1987 [AU] Australia .................. PI1067/87

[51] Int. Cl.$^6$ .................. D06P 5/00; D06M 13/00
[52] U.S. Cl. .................. 8/128.1; 8/405; 8/406; 8/501; 8/DIG. 13
[58] Field of Search .................. 8/128.1, 501, 405, 8/406, DIG. 13

[56] References Cited

U.S. PATENT DOCUMENTS

| | | | |
|---|---|---|---|
| 3,619,106 | 11/1971 | L'Oreal | 8/405 |
| 4,063,877 | 12/1977 | Elliot et al. | 8/102 |
| 4,293,543 | 10/1981 | Cotte et al. | 424/59 |
| 4,425,132 | 1/1984 | Grollier et al. | 8/405 |
| 4,615,709 | 10/1986 | Nakao | 8/599 |
| 4,663,158 | 5/1987 | Wolfram | 8/405 |
| 5,173,085 | 12/1992 | Brown et al. | 8/405 |
| 5,192,333 | 3/1993 | Lapidus | 8/405 |

FOREIGN PATENT DOCUMENTS

| | | |
|---|---|---|
| 0066438 | 9/1975 | Australia . |
| B6643874 | 9/1975 | Australia . |
| A3264378 | 8/1979 | Australia . |
| B3264278 | 8/1979 | Australia . |
| 4992379 | 5/1980 | Australia . |
| B4992379 | 5/1980 | Australia . |
| A6918187 | 8/1989 | Australia . |
| 2336475 | 12/1976 | France . |
| A2520700 | 11/1976 | Germany . |
| 54-140739 | 1/1979 | Japan . |
| 1444426 | 7/1976 | United Kingdom . |
| A1444426 | 7/1976 | United Kingdom . |
| 2031469 | 4/1980 | United Kingdom . |

OTHER PUBLICATIONS

Rapid Dyeing of Wool Without Damage, Hine et al., 1964.

Supplementary European Search Report 88 90 3132, Jun. 27, 1991, The Hague.

Journal of the Society of Dyers & Colourists, *The Influence of Amphoteric Products on the Affinity of Wool for Acid dyes*, vol. 103, Jan. 1987.

F.J. Harrigan & J.A. Rippon, "A New Method For Dyeing Wool At Low Temperature" Textile Institute 1988 World Conference (pp. 412–419).

J. Riva and J. Cegarra, The influence of amphoteric prodcuts on the affinity of wool for acid dyes Journal of the Society of Dyers & Colourists (1987) Jan. No. 1 pp. 34–37 Bradford Gr. Britain.

*Primary Examiner*—Jerry D. Johnson
*Attorney, Agent, or Firm*—Sughrue, Mion, Zinn, Macpeak & Seas, PLLC

[57] ABSTRACT

A method of applying an anionic dye to keratin fibers which involves pre-treating the fibers by contacting them with a solution of an amphoteric surfactant, and then applying the dye to the pre-treated fibers. A method of preparing keratin fibers for dyeing, printing, or other treatments by contacting the fibers with a solution containing an amphoteric surfactant but substantially no dye.

35 Claims, No Drawings

PROCESS FOR DYEING WOOL AND OTHER KERATIN FIBRES

BACKGROUND OF THE INVENTION

1. Field of the Invention

The present invention relates to the application of dye to keratin fibres, and to products incorporating such fibres.

2. Description of the Related Art

Wool and other keratinous fibres are usually dyed from acidic liquors that often contain various reagents, in addition to dyes. In conventional wool dyeing, the temperature of the dyebath is usually increased progressively to around 95°–100° C., where it is maintained for a time, up to several hours, that depends on the particular dyes that are being applied. These dyeing procedures can consume large amounts of energy. Furthermore, a significant degree of fibre damage can be caused, particularly if the pH of the dyebath is far removed from the iso-electric region of wool (ca pH 4–5). The object of the present invention is to enable wool to be dyed in fibre, yarn, fabric or garment form under milder conditions than are now commonly used. The milder conditions may be shorter times and/or lower temperatures than those usually required in conventional practice to give good levelling, exhaustion and fastness properties. This results in benefits in terms of less fibre damage, less yellowing and savings in time and energy consumption, compared with traditional methods. A further objective of this invention is to produce dyeings that are less skittery than those produced by alternative procedures. (Note: "skittery" is a term used to denote an uneven distribution of dye along a fibre.)

Anionic, cationic and amphoteric surfactants are used widely in the textile industry, as assistants for dyeing wool and other fibres by exhaustion methods. It is well known that the rate of exhaustion of dyes onto wool is enhanced by addition of certain surfactants to acidic dye liquors (see, for example, Hine, R. J. and McPhee, J. R., Rapid Dyeing of Wool Without Damage, Dyer, 132, p.523 (1964). The compounds that are most commonly used for this purpose are nonionic or amphoteric in nature; their addition to acidic dye liquors gives improvements in the rate of exhaustion and penetration into the fibre of many dyes. They also produce improvements in the appearance of the resultant dyeings, in terms of decreased skitteriness. These effects are utilised in low temperature dyeing procedures, in which wool is dyed at temperatures below the boil (usually 75°–90° C.).

SUMMARY OF THE INVENTION

The present invention is based on the unexpected observation that aqueous pretreatment of keratin fibres, such as wool, with an amphoteric surfactant, preferably under alkaline conditions, prior to addition of dyes, increases the rate of exhaustion, rate of penetration and overall uniformity of dyes applied from acidic dyebaths. The increased rate of penetration enables dyeings of excellent fastness properties and colour yield to be obtained at lower temperatures and/or in shorter times, compared with conventional practice. A feature of the present invention is that a differential dyeing effect is obtained when the pretreated wool is dyed in the same dyebath as untreated material. Treatment with an alkaline solution of an amphoteric surfactant, according to the method described herein, has also been found to provide an effective pretreatment for the application of dyes in the form of conventional print pastes to wool substrates. Thus, the surfactant/alkali treatement can be used instead of the chlorination procedures commonly employed in industry.

Furthermore, it has been found that the pretreatment can be applied to wool in the form of a paste containing the amphoteric surfactant, an alkali and thickening agent. The printed fabric is stored for a time between 1 min and 24 hr, precautions being taken to prevent the printed area from drying-out. After the chemicals have been washed from the fabric, the latter can be dyed immediately or dried and dyed later. When the fabric is dyed, a "tone-on-tone" effect is produced, with the printed regions dyed to a deeper shad than the base fabric.

The invention accordingly provides a method of preparing keratin fibres for dyeing, printing or other treatments comprising contacting the fibres with a solution, preferably aqueous, containing an amphoteric surfactant but substantially no dye.

The invention also provides a method of applying dye to keratin fibres comprising pretreating the fibres by contacting them with a solution, preferably aqueous, of an amphoteric surfactant, and thereafter applying dye to the pretreated fibres.

DESCRIPTION OF THE PREFERRED EMBODIMENT(S)

As extremely low concentrations of surfactant can improve dyeing properties of the fibres, there is no absolute lower limit for the amount of surfactant which needs to be used. However, for optimum results it is preferred that the weight of surfactant is at least equal to 0.1% of the weight of the fibre being treated.

An important feature of this invention is that the improvements in dyeing properties, obtained by pretreatment with an amphoteric surfactant, are superior to the well-known effects described above, obtained by adding amphoteric or nonionic surfactants directly to acidic dye liquors.

The pretreatment can be applied, for example, by a long liquor method, or by padding or printing. The dye can be applied by any suitable conventional technique, whether by way of simple dyeing or by way of printing.

The amphoteric surfactants used for the purposes of the present invention may contain a variety of cationic and anionic groups. The preferred type of cationic groups are amine salt, quaternary nitrogen, pyridinium or substituted imidazoline groups and the anionic groups are carboxyl, sulphate ester or sulphonic acid moieties. The amphoteric reagents can contain more than one type of cationic and/or anionic group; they may also contain other types of groupings that are neutral in character, for example hydrocarbon or alkylene oxide chains.

Particularly useful are the following types of amphoteric surfactants:

(a) N-alkyl betaines and sulphobetaines of the type:

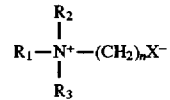

$R_1$, $R_2$ and $R_3$ are alkyl groups; $n \geq 1$; $X^-$ is either $-COO^-$ or $-SO_3^-$ (b) Alkyl-amide betaines and sulphobetaines of the type:

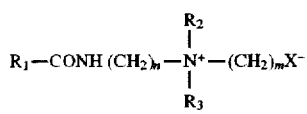

$R_1$, $R_2$ and $R_3$ are alkyl groups; $m \geq 1$; $n \geq 1$
$X^-$ is either $-COO^-$ or $-SO_3^-$ (c) Amphoteric surfactants of the following type:

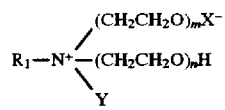

$R_1$ is an alkyl group, usually containing less than 22 Carbon atoms.

m and n are usually between 1 and 15.
$X^-$ is $-COO^-$; $-SO_3^-$; or $-OSO_3^-$
Y is an amide or other fatty acid derivative.

(d) Amphoteric surfactants of the following type:

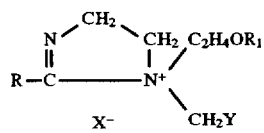

R is a fatty acid radical.
$R_1$ is H, Na or $CH_2COOM$.
X is OH, an acid salt or the salt of an anionic surface active sulphate or sulphonate.
Y is COOM, $CH_2COOM$ or

M is Na, H or an organic base.

Amphoteric surfactants are often supplied in mixtures that also contain other types of surfactants, e.g. nonionic, cationic or anionic.

Commercial products, containing amphoteric surfactants, that have been found to be effective include the following: Albegal B (Ciba-Geigy), Abegal SET (Ciba-Geigy), Avolan UL75 (Bayer), Avolan RE (Bayer), Keriolan A (CHT-T übingen), Leveller NR (Holliday), Lyogen FN (Sandoz), Transferin KW (Dr. TH. Böhme), Uniperol SE (BASF) and Remol GES (Hoechst). However, other amphoteric reagents and products containing these reagents, particularly those used in the dyeing of wool or nylon, are also suitable for use according to the method described in the present invention. The amount of surfactant required depends upon the percentage of the active constituent in the product; however, in general, this is in the range 0.1–20 g/l, when applied at a liquor ratio of 30:1.

As discussed above, the pretreatment is preferably carried out under alkaline conditions. Although some improvements in dyeing rate are obtained when wool is pretreated with amphoteric surfactants from acidic liquors, optimum results are obtained only when the pretreatment is carried out at an alkaline pH value. The most suitable pH values are in the range pH 7–11. The pH value of the pretreatment liquor can be set by any convenient method, using organic or inorganic reagents, or mixtures of these. It is convenient, although not essential, to use a buffered system because this ensures that the maximum degree of repoducibility of the effect is obtained. A particularly useful treatment pH is in the range pH 8–8.5, because this provides the optimum improvement in dyeing rate whilst minimising the possibility of alkaline degradation of the fibre.

The treatment can be carried out at any temperature in the range 5°–100° C. Temperatures that are particularly suitable are those commonly used for scouring wool, viz. 20°–50° C. Although any treatment time from one minute to several hours can be used, times of 10–60 mins. are particularly suitable.

An especially advantageous application of the invention is to wool fibres. An advantage of the process is that the treatment can be included in the normal sequence of wool processing. For example, as a pretreatment prior to the dyeing of loose stock, sliver, top, yarn, or fabric, the latter including fabric in the form of garments. The treatment can also be applied as part of the final stages of raw wool scouring. Application of the dye to a fabric can be in the form of a print paste, whereby to produce a print on the fabric. The method may comprise the further step of dyeing the printed fabric.

A further advantage of this invention is that the treated material can be dyed immediately, or dried and dyed at some later time, without any loss of the effect. The fibres may be pretreated as, e.g. raw scoured wool fibres or yarn, and incorporated into a fabric between said pretreatment and said application of dye to the fibres.

All classes of dyes used for the colouration of keratin fibres may be used; e.g. acid levelling, acid milling, 1:1 premetallised, 1:2 premetallised, chrome, reactive and vat dyes.

The keratin fibres that can be treated will normally be new or reprocessed wool from sheep. This can include wool that has been modified, for example, by a shrink-resist or other treatment. The keratin fibres may, however, also be derived from the following sources: alpaca, angora, cashmere, mohair, vicuna, guanaco, rabbit, camel, llama or human hair; or blends of these fibres with the wool from sheep. The material may consist wholly of keratinous fibres, or of blends with synthetic fibrous and filamentary material, or with natural or regenerated cellulosic fibres.

In the case of human hair, the pretreatment is preferably carried out under neutral or slightly alkaline conditions, at room temperature. It may be applied either after shampooing, or as part of a shampooing procedure. In either case, the amphoteric surfactant is advantageously left in contact with the hair for 5–60 min, before rinsing. The pretreated hair is then dyed with a suitable formulation used for colouration. The advantage of the pretreatment is an improvement in the penetration of the hair dye and hence better colour yield and fastness to shampooing, compared with untreated hair.

The invention is illustrated by the following examples.

EXAMPLE 1

Samples of a pure wool, woven worsted fabric were treated, at a liquor:goods ratio of 28:1, for 2 hours at 40° C. with solutions of Albegal B (1 g/l), set to various pH values by means of "Universal" buffer (A Textbook of Quantitative Inorganic Analysis, A. I. Vogel, Longmans, Green and Co. (1951), p. 872). The samples were rinsed with water and then dyed, at 40° C. and a liquor ratio of 28:1, with C. I. Acid Red 18 (1% oww). The dyebaths were buffered to pH 4.5 with sodium acetate and acetic acid. Dyebath exhaustions were measured spectrophotometrically. The rates of exhaustion, expressed in terms of time to 50% exhaustion ($T_{1/2}$), and the dyebath exhaustion after 120 min. ($E_{120}$) are shown in Table 1. Also shown, for comparison, are the values for the above parameters, obtained for wool fabrics treated with the buffer solutions, only.

TABLE 1

| pH of pretreatment | Buffer & Albegal B | | Buffer only | |
|---|---|---|---|---|
| liquor | $T_{1/2}$ (min) | $E_{120}$ (%) | $T_{1/2}$ (min) | $E_{120}$ (%) |
| 4 | 170 | 40 | 200 | 37 |
| 5 | 120 | 50 | 200 | 30 |
| 6 | 62 | 78 | 195 | 32 |
| 7 | 43 | 95 | 160 | 42 |
| 8 | 43 | 96 | 195 | 35 |
| 9 | 40 | 94 | 150 | 44 |
| 10 | 38 | 93 | 160 | 31 |

Untreated fabric $T_{1/2}$=200 min
$E_{120}$=40%

The fabrics pretreated with Albegal B were superior, in terms of higher colour yield and lower skitteriness, compared with those pretreated with the buffer alone. The improvements were most marked for the samples pretreated at pH values of 7 and above.

EXAMPLE 2

Samples of a pure wool woven worsted fabric were treated for various times at 40° or 50° C. and a liquor:goods ratio of 28:1, with an aqueous liquor of the following composition: Albegal B (2% product oww), disodium hydrogen phosphate (1.6 g/l) and sodium dihydrogen phosphate (0.1 g/l). The pH value of the liquor varied from 8.2 to 8.0 during the course of the treatment. The samples were rinsed with water and dyed, as described in Example 1. The dye exhausted more rapidly onto the treated fabrics compared with untreated wool, as shown by the values for the times to 50% exhaustion ($T_{1/2}$) and the dye liquor exhaustions after 120 min ($E_{120}$) in Table 2.

TABLE 2

| Pretreatment Time | Pretreatment Temp. 40° C. | | Pretreatment Temp. 50° C. | |
|---|---|---|---|---|
| (min) | $T_{1/2}$ (min) | $E_{120}$ (min) | $T_{1/2}$ (min) | $E_{120}$ (min) |
| 0 | 200 | 35 | 200 | 35 |
| 5 | 75 | 80 | 70 | 85 |
| 15 | 48 | 92 | 44 | 89 |
| 30 | 40 | 96 | 36 | 97 |
| 60 | 32 | 99 | 32 | 99 |
| 120 | 28 | 100 | 28 | 100 |

After rinsing and drying, it was apparent that the pretreated, dyed fabrics had a higher colour yield and were less skittery than the untreated, dyed samples.

EXAMPLE 3

It is well know in the prior art that addition of amphoteric or nonionic surfactants to dyebaths increases the rate of uptake of dyes by wool. However, the improvements in dyeing rate obtained by treatments carried out according to the present invention are greater than those obtained by addition of surfactant to the dyebath. This is illustrated by the following example.

Samples of the wool fabric were treated, at a liquor:goods ratio of 28:1, for 30 min at 40° C. in an aqueous solution of Albegal B (2% product oww). The solution was buffered to pH 8–8.2 as described in Example 2. The samples were rinsed and then the treated samples, and also untreated controls, were dyed as described in Example 1. Surfactants were added to the dyebaths as indicated in Table 3, which also shows the rates of exhaustion of the liquors (expressed in terms of $T_{1/2}$).

TABLE 3

| | $T_{1/2}$ (min) | |
|---|---|---|
| Surfactant added to dyebath | Untreated fabric | Fabric pretreated with Albegal B |
| None | 200 | 49 |
| 0.5% oww Nonionic (a) | 126 | 48 |
| 1.0% oww Nonionic (a) | 110 | 45 |
| 2.0% oww Nonionic (a) | 109 | 50 |
| 0.5% oww Albegal B | 113 | 56 |
| 1.0% oww Albegal B | 108 | 54 |
| 2.0% oww Albegal B | 100 | 58 |

(a) A nonylphenol/ethylene oxide condensate, containing an average of 8 moles of ethylene oxide per mole of nonylphenol.

EXAMPLE 4

This example illustrates that improvements in the rate of uptake of dyes by wool, produced by the amphoteric surfactant/alkali treatments of the present invention, are also obtained when the wool is dyed at 90° C.

Also demonstrated is the superiority of the new pretreatments compared with the effects of adding a surfactant to the dye liquor, according to the previously known methods for dyeing wool at low temperatures (see, for example, the work of Hine and McPhee described in, Dyer, 132, p.523 (1964).

Samples of the wool fabric were treated with an aqueous solution of Albegal B, as described in Example 3. The samples were rinsed and then dyed with Lanasol Blue 3G (Ciba-Geigy) (1% oww), from liquors set at pH 4.5 with a sodium acetate/acetic acid buffer. Where indicated in Table 4, the dyebaths also contained the nonionic surfactant, Lissapol TN450 (ICI). The temperature of the dyebath was held at 40° C. for 10 min and then increased to 90° C. over a period of 60 min, where it was held for a further 40 min. The samples were removed from the liquor, rinsed and dried.

TABLE 4

| | $T_{1/2}$ (min) | |
|---|---|---|
| Surfactant added to dyebath | I Untreated fabric | II Fabric pretreated with Albegal B |
| None | 48 | 29 |
| 0.5% oww Lissapol TN450 | 37 | 27 |

The dyeings on the pretreated fabrics (column II) were of better colour yield and of less skittery appearance than the control samples (column I).

EXAMPLE 5

A sample of the wool fabric was treated for 30 min with Albegal B, as described in Example 1. The fabric was rinsed, dried and then stored for one week before re-wetting and dyeing, as described in Example 1. The value for $T_{1/2}$ obtained for the pretreated and dried fabric was identical to the value obtained for a sample pretreated in a similar manner with Albegal B, but dyed immediately without intermediate drying. Furthermore, the quality of the dyeing on the pretreated fabric was equal to that on a fabric dyed immediately after the pretreatment. Thus, intermediate drying and storage are not detrimental to the beneficial effects of the treatment.

EXAMPLE 6

Samples of the wool fabric were treated, at a liquor:goods ratio of 28:1, for 2 hours at 40° C. with solutions containing Compound (I) (1.7 g/l).

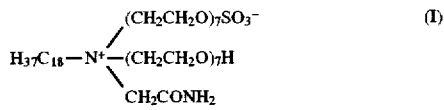

The solutions were adjusted to pH 8 with sodium carbonate or ammonium hydroxide. During the course of the treatments, the liquors were maintained at pH 8 by further additions of the above alkaline reagents. The samples were rinsed and dyed, as described in Example 1.

TABLE 5

| Treatment liquor additive | $T_{1/2}$ (min) | | $E_{120}$ (%) | |
|---|---|---|---|---|
| | Alkali Only | Alkali + Compound I | Alkali Only | Alkali + Compound I |
| Sodium Carbonate | 190 | 32 | 32 | 96 |
| Ammonium Hydroxide | 180 | 40 | 32 | 93 |
| Untreated | | 200 | | 40 |

The values for $T_{1/2}$ and $E_{120}$ in Table 5 show that the surfactant-pretreated samples were superior, with respect to dyeing rate and final exhaustion, compared with untreated or alkali-treated wool.

EXAMPLE 7

Samples of the wool fabric were treated, at a liquor ratio of 28:1 for 30 min at 40° C., in solutions containing 5 g/l of the various proprietary compounds listed in Table 6. The solutions were set to pH 8 with the phosphate buffer mixture described in Example 2. The samples were rinsed and dyed as described in Example 1.

TABLE 6

| Compound | $T_{1/2}$ (min) | $E_{120}$ (%) |
|---|---|---|
| None | 200 | 29 |
| Albegal SET (Ciba-Geigy) | 124 | 49 |
| Lyogen FN (Sandoz) | 54 | 81 |
| Avolan UL75 (Bayer) | 74 | 66 |
| Leveller NR (Holliday) | 57 | 81 |
| Keriolan A (CHT Tübingen) | 70 | 71 |
| Transferin KW (Th Böhme) | 45 | 84 |
| Avolan RE (Bayer) | 82 | 66 |
| Remol GES (Hoechst) | 60 | 78 |
| Uniperol SE (BASF) | 35 | 92 |

Table 6 indicates that the pretreatment increased the rate of exhaustion of the dyes, and also increased the equilibrium exhaustion obtained for a dyeing time of 120 min. In all cases the dyeings were more level and less skittery than similar dyeings on untreated fabric.

EXAMPLE 8

A sample of the wool fabric was treated, at a liquor ratio of 28:1, for 30 min at 40° C. with a solution of Albegal B (2% oww). The solution was set to pH 8 with the phosphate buffer mixture described in Example 2. The sample was rinsed and then dyed at pH 4.5 and 70° C. with Lanasol Red 6G (Ciba-Geigy) (1% oww). A level dyeing of good penetration was obtained. The dye liquor was completely exhausted within 20 min, compared with only 36% exhaustion for an untreated sample.

EXAMPLE 9

Samples of the wool fabric were treated for 60 min at 40° C., as described in Example 8, and then rinsed with water. The treated fabrics, and also untreated samples, were dyed with the dyes indicated in Table 7 by the following method. The bath was set at pH 4.5 with a sodium acetate/acetic acid buffer and the dyeing commenced at 40° C. After 20 min at 40° C., the temperature of the dye liquor was increased to 80° C. over a period of 70 min. The dyebath was maintained at 80° C. for 30 min and then the samples were rinsed and dried in the usual manner.

TABLE 7

| | ISO3 Wash Test | | | | | | | |
|---|---|---|---|---|---|---|---|---|
| | Shade | | | | Crocking Fastness* | | | |
| | Change | | Cotton Stain | | Dry | | Wet | |
| Dye | Unt. | Pre-tr. | Unt. | Pre-tr. | Unt. | Pre-tr. | Unt. | Pre-tr. |
| Acidol Red MBR | 4 | 4–5 | 4–5 | 5 | 4–5 | 4–5 | 3–4 | 3–4 |
| Carbolan Blue BS | 4–5 | 4–5 | 4–5 | 5 | 5 | 5 | 4–5 | 4–5 |
| Lanasol Red 6G | 5 | 5 | 5 | 5 | 4–5 | 5 | 4–5 | 4–5 |

*Measured by AATCC TM 8-1981

The pre-treated samples were evenly dyed and were less skittery than the untreated controls. Furthermore, as shown in Table 7, the dyeings on the pretreated wool were of good fastness to washing and rubbing.

EXAMPLE 10

A sample of wool fabric was treated at a liquor ratio of 28:1, for 30 min at 40° C. and pH 8–8.2, with the sulphobetaine, N-hexadecyl-N, N-dimethyl-3-amino-1-propane sulphonic acid (1% oww). The sample was rinsed and dyed at pH 4.5 and 40° C. with C.I. Acid Red 18 (1% oww), by the method described in Example 1. The values for $T_{1/2}$ and $E_{120}$ of 70 min and 68%, respectively, show that the pretreatment increased both dyeing rate and final exhaustion, compared with untreated wool (the values for untreated wool were 200 min and 40%, respectively).

EXAMPLE 11

A sample of wool fabric was treated with a solution containing 5 g/l of either an alkyl betaine (Compound II) or an alkylamido propyl dimethylamine betaine (Compound III). The treatment conditions were as described in Example 10. The samples were then dyed, also by the method described in Example 10.

-continued

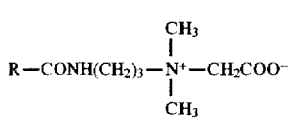

COMPOUND III

In both cases, R is predominantly $C_{12}/C_{14}$

TABLE 8

|  | $T_{1/2}$ (min) | $E_{120}$ (%) |
| --- | --- | --- |
| Compound II | 83 | 62 |
| Compound III | 57 | 80 |
| Untreated | 200 | 40 |

The results in Table 8 show that alkyl betaines and alkyl amido betaines can be used, according to the present invention, to improve the dyeing properties of wool.

EXAMPLE 12

Samples of the wool fabric were treated, at a liquor ratio of 28:1 for 30 min at 40° C., in solutions containing 5 g/l of the compounds listed in Table 9. The solutions were set to pH 8 with the phosphate buffer described in Example 2. The samples were rinsed and dyed as described in Example 1.

TABLE 9

| Compound | Commercial Name | $T_{1/2}$ (min) | $E_{120}$ (%) |
| --- | --- | --- | --- |
| Triethanolamine salt of N-lauryl-myristyl-β-aminopropionic acid | — | 86 | 63 |
| Sodium salt of N-lauryl-myristyl-β-aminopropionic acid | — | 57 | 67 |
| N—R-β-aminobutyric acid | Armeen Z (Akzo Chemicals Ltd) | 57 | 79 |
| $[R-C-NCH_2CH_2N(CH_2OH)(CH_2COONa)]^+ OH^-$ | Miranol CM conc. (Miranol Chemical Co) | 86 | 65 |
| $[C_{11}H_{23}C-NCH_2CH_2N(C_2H_4OH)(CH_2COONa)]^+ OH^-$ | Miranol HM conc. (Miranol Chemical Co) | 22 | 97 |
| $[C_{17}H_{33}C-NCH_2CH_2N(C_2H_4OH)(CH_2COONa)]^+ OH^-$ | Miranol CM-SF conc. (Miranol Chemical Co) | 79 | 64 |

Note: R is coco fatty acid

The results in Table 9 show that pretreatment with the various amphoteric surfactants increased the dyeing rate and equilibrium exhaustion.

EXAMPLE 13

A sample of a pure wool, woven fabric was treated at a liquor ratio of 28:1, with an aqueous solution of Albegal B (2 g/l) for 30 min at 40° C. The solution was buffered to pH 8–8.2 as described in Example 2. After rinsing and drying, a design was printed onto the fabric with a paste of the following composition:

5% (w/w) urea
5% (w/w) thiodiglycol
5% (w/w) Indalca PA-3 (Cesalpinia)
2% (w/w) Carbolan Blue BS (ICI)
83% (w/w) water The printed fabric was dried, steamed for 30 min at 100° C. and washed-off for 15 min at 40° C. in an aqueous solution of Aerosol OT (Cyanamid) (5 g/l) and 0.880 ammonium hydroxide (5 g/l), dried and pressed. The print on the pretreated fabric was deeper and of less skittery appearance, compared with a print on untreated wool.

EXAMPLE 14

A sample of 2/28's worsted yarn was treated, at a liquor ratio of 15:1, for 30 min at 40° C. with an aqueous solution of Albegal B (2% oww). The solution was buffered to pH 8–8.2, as described in Example 2. The yarn was rinsed several times with water and dried.

A fabric was knitted, consisting of alternate stripes (2 cm wide) of pretreated and untreated (scoured only) yarn. The fabric was dyed with Lanasol Red 6G, according to the method described in Example 8. A differential dyeing effect was obtained, with the portions of the fabric constructed from the pretreated yarn being more deeply dyed than the parts knitted from untreated yarn.

EXAMPLE 15

A design was printed onto a pure wool fabric with a paste of the following composition:

2% (w/w) Albegal B
0.2% (w/w) Sodium carbonate
5% (w/w) Solvitosegum OFA (Avebe)
92.8% (w/w) water.

The fabric was covered with polythene, to prevent the printed area from drying out, and stored for 60 min at room temperature. The fabric was washed-off in warm water containing acetic acid (1 g/l) and then dyed with Acidol Brilliant Blue M5G (1% oww) at pH 4.5. The dyebath was heated from 40° C. to 85° C. at 1° C./min and held at the latter temperature for 30 min. The sample was rinsed and dried. The printed design was dyed more deeply than the remainder of the fabric (i.e. a "tone-on-tone" effect).

I claim:

1. A method of applying an anionic dye to keratin fibres which comprises pretreating the fibres by contacting them with an alkaline solution of an amphoteric surfactant, said solution having a pH of not greater than 11, and thereafter applying dye to the pretreated fibres as an acidic dye medium.

2. A method according to claim 1 wherein said alkaline solution has a pH in the range of 8 to 8.5.

3. A method according to claim 1 wherein the surfactant is present in the amount of at least 0.1% w/w with respect to the fibres.

4. A method according to claim 1 wherein said pretreatment is carried out at a temperature in the range of 5° to 100° C.

5. A method according to claim 4 wherein said pretreatment is carried out at a temperature in the range of 20° to 50° C.

6. A method according to claim 1 wherein said pretreatment is carried out for a period in the range of 10 to 60 mins.

7. A method according to claim 1 wherein said solution is an aqueous solution.

8. A method according to claim 1 wherein said amphoteric surfactant contains cationic groups selected from the group consisting of amine salt, quaternary nitrogen, pyridinium and substituted imadizoline groups, and further contains anionic groups selected from the group consisting of carboxyl, sulphate ester and sulphonic acid moiety groups.

9. A method according to claim 1 wherein said amphoteric surfactant is selected from:

(a) N - alkyl betaines and sulphobetaines of the formula:

$$R_1 - \overset{\overset{R_2}{|}}{\underset{\underset{R_3}{|}}{N^+}} - (CH_2)_n X^-$$

$R_1$, $R_2$, and $R_3$ are alkyl groups; $n \geq 1$; $X^-$ is either $-COO^-$ or $-SO_3^-$;

(b) alkyl amide betaines and sulphobetaines of the formula:

$$R_1 - CONH(CH_2)_n - \overset{\overset{R_2}{|}}{\underset{\underset{R_3}{|}}{N^+}} - (CH_2)_m X^-$$

$R_1$, $R_2$, and $R_3$ are alkyl groups; $m \geq 1$; $n \geq 1$; $X^-$ is either $-COO^-$ or $-SO_3^-$;

(c) surfactants of the formula:

$$R_1 - N^+ \underset{Y}{\overset{(CH_2CH_2O)_m X^-}{\diagup}} (CH_2CH_2O)_n H$$

$R_1$ is an alkyl group, containing less than 22 carbon atoms;

m and n are between 1 and 15;

$X^-$ is $-COO^-$; $SO_3^-$; or $-OSO_3^-$;

Y is an amide or fatty acid derivative; and (d) surfactants of the formula:

$$\underset{X^-}{\overset{R-\overset{\overset{O}{\|}}{C}-}{}}\underset{}{N}\overset{CH_2}{\underset{\underset{CH_2Y}{}}{\diagdown}}\overset{CH_2 \; C_2H_4OR_1}{\underset{N^+}{\diagup}}$$

R is a fatty acid radical;

$R_1$ is H, Na or $CH_2COOM$;

X is OH, an acid salt or the salt of an anionic surface active sulphate or sulphonate;

Y is COOM, $CH_2COOM$ or $$\underset{OH}{\overset{}{\underset{|}{CHCH_2SO_3M}}};$$

M is Na, H or an organic base.

10. A method according to claim 1 wherein the fibres are wool fibres.

11. A method according to claim 10 wherein the fibres are in a fabric.

12. A method according to claim 11 wherein the dye is applied to the pretreated fibres of the fabric in the form of a print paste, to thereby produce a print on the fabric.

13. A method according to claim 12 comprising further dyeing the printed fabric.

14. A method according to claim 12 wherein the wool fibres are pretreated while raw scoured fibres or while in a yarn.

15. A method according to claim 1 wherein the fibres are incorporated into a fabric between said pretreatment and said application of dye to the fibres.

16. A method of preparing keratin fibers for the application to said keratin fibers of dye as an acidic dye medium, which method of preparing comprises contacting the fibres with an alkaline solution containing an amphoteric surfactant but substantially no dye, said solution having a pH of not greater than 11.

17. A method according to claim 16 wherein said alkaline solution has a pH in the range of 8 to 8.5.

18. A method according to claim 16 wherein the surfactant is present in the amount of at least 0.1% w/w with respect to the fibres.

19. A method according to claim 16, carried out at a temperature in the range of 5° to 100° C.

20. A method according to claim 19, carried out at a temperature in the range of 20° to 50° C.

21. A method according to claim 16, carried out for a period in the range of 10 to 60 mins.

22. A method according to claim 16 wherein said solution is an aqueous solution.

23. A method according to claim 16, wherein said amphoteric surfactant contains cationic groups selected from the group consisting of amine salt, quaternary nitrogen, pyridinium and substituted imadizoline groups, and further contains anionic groups selected from the group consisting of carboxyl, sulphate ester and sulphonic acid moiety groups.

24. A method according to claim 16 wherein the fibres are wool fibres.

25. A method according to claim 24 wherein the wool fibres are in a fabric.

26. A method of applying dye to keratin fibres which comprises pretreating the fibres by contacting them with an aqueous alkaline solution of an amphoteric surfactant, which solution has a pH of not greater than 11, and thereafter applying dye as an acidic medium to the pretreated fibres, wherein the surfactant is present in an amount of at least 0.1% w/w with respect to the fibres, wherein the pretreatment is carried out at a temperature in a range of 5° to 100° C., and wherein said amphoteric surfactant contains cationic groups from amine salt, quaternary nitrogen, pyridinium, or substituted imidazoline groups and further contains anionic groups from carboxyl, sulfate, ester, or sulfonic acid moiety groups.

27. A method according to claim 26, wherein said pretreatment is carried out at a temperature in the range of 20° to 50° C.

28. A method according to claim 26, wherein said pretreatment is carried out for a period in the range of 10 to 60 mins.

29. A method according to claim 26, wherein said amphoteric surfactant is selected from:

(a) N - alkyl betaines and sulphobetaines of the formula:

$$R_1-\overset{\overset{R_2}{|}}{\underset{\underset{R_3}{|}}{N^+}}-(CH_2)_nX^-$$

$R_1$, $R_2$, and $R_3$ are alkyl groups; $n \geq 1$; $X^-$ is either $-COO^-$ or $-SO_3^-$;

(b) alkyl amide betaines and sulphobetaines of the formula:

$$R_1-CONH(CH_2)_n-\overset{\overset{R_2}{|}}{\underset{\underset{R_3}{|}}{N^+}}-(CH_2)_mX^-$$

$R_1$, $R_2$, and $R_3$ are alkyl groups; $m \geq 1$; $n \geq 1$; $X^-$ is either $-COO^-$ or $-SO_3^-$;

(c) surfactants of the formula:

$$R_1-N^+\underset{Y}{\overset{(CH_2CH_2O)_mX^-}{{-(CH_2CH_2O)_nH}}}$$

$R_1$ is an alkyl group, containing less than 22 carbon atoms;

m and n are between 1 and 15;

$X^-$ is $-COO^-$; $SO_3^-$; or $-OSO_3^-$;

Y is an amide or fatty acid derivative; and (d) surfactants of the formula:

$$\begin{array}{c} N\overset{CH_2}{\diagup}\!\diagdown\\ R-C\overset{\|}{\phantom{x}}\underset{X^-}{\phantom{xxxx}}N^+\overset{CH_2\ C_2H_4OR_1}{\diagup}\\ \diagdown CH_2Y \end{array}$$

R is a fatty acid radical;

$R_1$ is H, Na or $CH_2COOM$;

X is OH, an acid salt or the salt of an anionic surface active sulphate or sulphonate;

Y is COOM, $CH_2COOM$ or $$\underset{OH}{\overset{CHCH_2SO_3M;}{|}}$$

M is Na, H or an organic base.

30. A method according to claim 26, wherein the fibres are wool fibres.

31. A method of preparing keratin fibres for dyeing with the application of dye as an acidic dye medium, which method comprises contacting the fibres with an aqueous alkaline solution containing an amphoteric surfactant, but substantially no dye, said solution having a pH of not greater than 11, wherein the surfactant is present in an amount of at least 0.1 w/w with respect to the fibres, the contacting is carried out at a temperature in the range of 5° to 100° C., and wherein said amphoteric surfactant contains cationic groups selected from amine salt, quaternary nitrogen, pyridinium, or substituted imidazoline groups, and further contains anionic groups selected from carboxyl, sulphate ester, or sulfonic acid moiety groups.

32. A method according to claim 31, carried out at a temperature in the range of 20° to 50° C.

33. A method according to claim 31, carried out for a period in the range of 10 to 60 mins.

34. A method according to claim 31, wherein the fibres are wool fibres.

35. A method according to claim 31, wherein said amphoteric surfactant is selected from:

(a) N - alkyl betaines and sulphobetaines of the formula:

$$R_1-\overset{\overset{R_2}{|}}{\underset{\underset{R_3}{|}}{N^+}}-(CH_2)_nX^-$$

$R_1$, $R_2$, and $R_3$ are alkyl groups; $n \geq 1$; $X^-$ is either $-COO^-$ or $-SO_3^-$;

(b) alkyl amide betaines and sulphobetaines of the formula:

$$R_1-CONH(CH_2)_n-\overset{\overset{R_2}{|}}{\underset{\underset{R_3}{|}}{N^+}}-(CH_2)_mX^-$$

$R_1$, $R_2$, and $R_3$ are alkyl groups; $m \geq 1$; $n \geq 1$; $X^-$ is either $-COO^-$ or $-SO_3^-$;

(c) surfactants of the formula:

$$R_1-N^+\underset{Y}{\overset{(CH_2CH_2O)_mX^-}{{-(CH_2CH_2O)_nH}}}$$

$R_1$ is an alkyl group, containing less than 22 carbon atoms;

m and n are between 1 and 15;

$X^-$ is $-COO^-$; $SO_3^-$; or $-OSO_3^-$;

Y is an amide or fatty acid derivative; and (d) surfactants of the formula:

$$\begin{array}{c} N\overset{CH_2}{\diagup}\!\diagdown\\ R-C\overset{\|}{\phantom{x}}\underset{X^-}{\phantom{xxxx}}N^+\overset{CH_2\ C_2H_4OR_1}{\diagup}\\ \diagdown CH_2Y \end{array}$$

R is a fatty acid radical;

$R_1$ is H, Na or $CH_2COOM$;

X is OH, an acid salt or the salt of an anionic surface active sulphate or sulphonate;

Y is COOM, $CH_2COOM$ or $$\underset{OH}{\overset{CHCH_2SO_3M;}{|}}$$

M is Na, H or an organic base.

* * * * *